US00PP25585P3

(12) United States Plant Patent
Volmary

(10) Patent No.: US PP25,585 P3
(45) Date of Patent: May 26, 2015

(54) ***FUCHSIA* PLANT NAMED 'FWUWW22-0'**

(50) Latin Name: ***Fuchsia* hybrid**
Varietal Denomination: FWUWW22-0

(71) Applicant: Hubertus Volmary, Munster (DE)

(72) Inventor: Hubertus Volmary, Munster (DE)

( * ) Notice: Subject to any disclaimer, the term of this patent is extended or adjusted under 35 U.S.C. 154(b) by 154 days.

(21) Appl. No.: 13/815,431

(22) Filed: Feb. 28, 2013

(65) Prior Publication Data

US 2014/0245513 P1 Aug. 28, 2014

(51) Int. Cl.
*A01H 5/02* (2006.01)

(52) U.S. Cl.
CPC ..... *A01H 5/02* (2013.01)
USPC ..... Plt./300

(58) Field of Classification Search
USPC ..... Plt./300
See application file for complete search history.

*Primary Examiner* — Anne Grunberg
(74) *Attorney, Agent, or Firm* — Cassandra Bright

(57) ABSTRACT

A new and distinct *Fuchsia* cultivar named 'FWUWW22-0' is disclosed, characterized a compact, upright plant habit, with a large number of flowers, with at least 2 flowers at every axil. Flowers have a very light pink calyx and white corolla, face outward, and flowering response is not dependent upon day length. The new variety is a *Fuchsia*, typically produced as a garden or container plant.

2 Drawing Sheets

Figure 1:
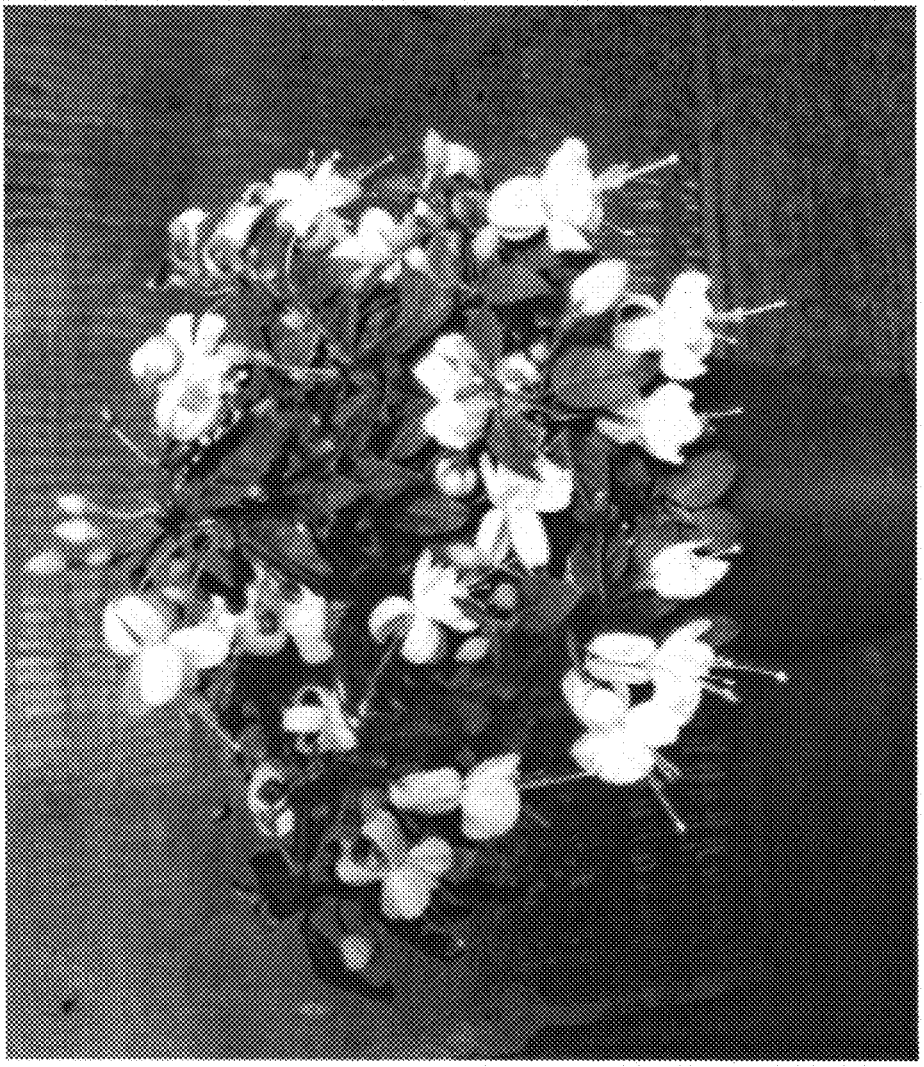

Latin name of the genus and species: *Fuchsia* hybrid.
Variety denomination: 'FWUWW22-0'.

BACKGROUND OF THE INVENTION

The new cultivar is a product of a planned breeding program. The new variety originated from a cross pollination of the seed parent, an unnamed, unpatented proprietary selection of *Fuchsia* hybrid with the pollen parent a different unnamed, unpatented *Fuchsia* hybrid. The crossing was made during the Summer of 2009, at a research greenhouse in Munster, Germany. 'FWUWW22-0' was discovered by the inventor, Hubertus Volmary, a citizen of Germany, at the same research greenhouse during the Spring of 2010.

Asexual reproduction of the new cultivar 'FWUWW22-0' was first performed in Munster Germany, at a commercial greenhouse by vegetative cuttings in Summer of 2010. 'FWUWW22-0' has since produced several generations and has shown that the unique features of this cultivar are stable and reproduced true to type.

SUMMARY OF THE INVENTION

The cultivar 'FWUWW22-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWUWW22-0.' These characteristics in combination distinguish 'FWUWW22-0' as a new and distinct *Fuchsia* cultivar:

1. Compact and upright plant habit.
2. Highly floriferous plants.
3. Flowering response not dependent upon day length.
4. Distinctive pastel pink calyx with white corolla.
5. Double flowers.
6. Flowers more outwardly facing than pendulous.
7. 2 or more flowers emerging from each axil.

PARENT COMPARISON

Plants of the new cultivar 'FWUWW22-0' are similar to plants of the seed parent in most horticultural characteristics, however, plants of the new cultivar differ in the following:

1. The new variety has a more upright plant habit.
2. The new variety has a light pink calyx, compared to a white calyx.
3. The new variety has double flowers, compared to single flowers.

Plants of the new cultivar 'FWUWW22-0' are similar to plants of the pollen parent in most horticultural characteristics, however, plants of the new cultivar differ in the following:

1. The new variety has a more upright plant habit.
2. The new variety has a more compact plant habit.
3. The new variety has more flowers per plant.
4. The new variety has many more lateral branches per plant.
5. The new variety has a white corolla, compared to a pink corolla.

COMMERCIAL COMPARISON

Plants of the new cultivar 'FWUWW22-0' are similar to plants of the commercial variety *Fuchsia* 'Snowy Summit', unpatented, in most horticultural characteristics, however, plants of the new cultivar differ in the following:

1. The new variety has a more upright plant habit.
2. The new variety has a more compact plant habit.
3. The new variety has more flowers per plant.
4. The new variety has many lateral branches per plant.
5. The new variety has smaller flowers.
6. Flowers of the new variety are more outwardly facing, whereas flowers of 'Snowy Summit' are pendulous.

Plants of the new cultivar 'FWUWW22-0' are similar to plants of the commercial variety *Fuchsia* 'White King', unpatented, in most horticultural characteristics, however, plants of the new cultivar differ in the following:

1. The new variety has a more upright plant habit.
2. The new variety has a more compact plant habit.
3. The new variety has more flowers per plant.
4. The new variety has many more lateral branches per plant.
5. The new variety has smaller flowers.
6. Flower of the new variety are more outwardly facing, whereas flowers of 'White King' are pendulous.

BRIEF DESCRIPTION OF THE PHOTOGRAPHS

The accompanying photograph in FIG. 1 illustrates in full color a typical plant of 'FWUWW22-0' grown outdoors in Santa Paula, Calif. This plant is approximately 30 weeks old, shown in a 1 gallon pot.

Figure 2:
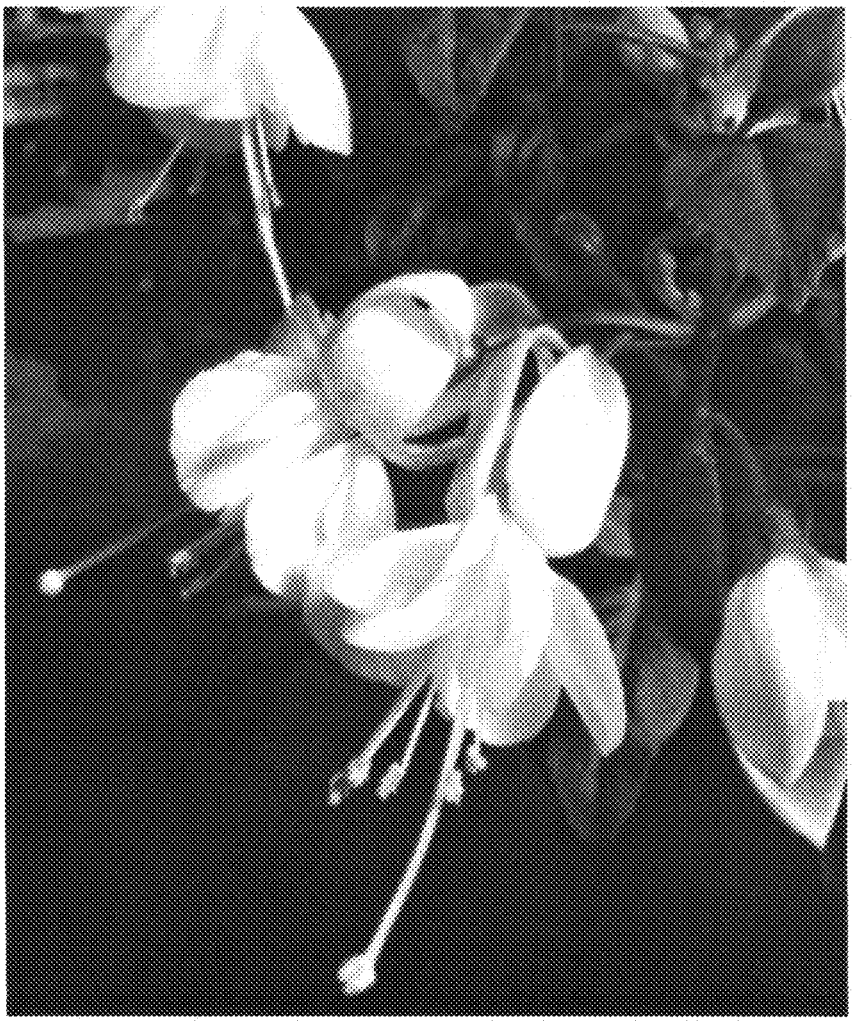

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001, except where general terms of ordinary dictionary significance are used. The following observations and measurements describe 'FWUWW22-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWUWW22-0'.

PROPAGATION

Propagation method: Vegetative Cuttings.
Time to initiate roots: About 2 weeks at 15° C. to 22° C.
Root description: Fine, densely fibrous.

PLANT

Age of plant described: Approximately 30 weeks from a rooted cutting.
Pot size of plant described: 1 gallon.
Height: Approximately 22 cm from soil line of pot to top of foliar and uppermost flowering plane.
Plant spread: Approximately 35 cm.
Growth rate: Rapid.
Growth habit: Upright, compact.
Branching characteristics: Free branching.
Length of primary lateral branches: Average 15 cm.
Diameter of lateral branches: Approximately 0.5 cm.
Quantity of primary lateral branches: Approximately 30.
Characteristics of primary lateral branches:
- *Color*.—Near RHS Greyed-Red N181 C.
- *Texture*.—Glabrous.
- *Strength*.—Strong, flexible.

Internode length: Average 1.4 cm.

FOLIAGE

Leaf:
- *Arrangement*.—Opposite.
- *Quantity*.—Approximately 12 to 16 fully expanded leaves per primary lateral branch.
- *Average length*.—4.9 cm.
- *Average width*.—2.3 cm.
- *Shape of blade*.—Ovate.
- *Apex*.—Acute.
- *Base*.—Oblique.
- *Margin*.—Shallowly crenate.
- *Texture of top surface*.—Glabrous.
- *Texture of bottom surface*.—Glabrous.
- *Aspect*.—Slightly cupped upward along margins, and overall slight reflex downward over the entire leaf blade.
- *Color*.—Young foliage upper side: Near RHS Green 137A. Young foliage under side: Near RHS Green 137B. Mature foliage upper side: Near RHS Green 137A. Mature foliage under side: Near RHS Green 137C.
- *Venation*.—Type: Pinnate. Venation color upper side: Near RHS Green 143C. Venation color under side: Near RHS Green 143D.
- *Attachment*.—Stalked.
- *Petiole*.—Length: Average 0.9 cm. Diameter: Average 0.15 cm. Texture: Pubescent. Color: Upper surface: Near RHS Yellow-Green 144A. Lower surface: Near RHS Green 138A.

FLOWER

Natural flowering season: Year round under temperate conditions. Flowering is not dependent upon day length.
Inflorescence and flower type and habit: At least 2 flowers emerge singly from each axil. Flowers emerge at different times, resulting in flowers of different maturity at each axil. Flowers are symmetrical and composed of a corolla surrounded by a decorative fused calyx. Flowers face outwardly.
Flowers per plant: Approximately 45 fully open flower and 80 buds on a mature plant.
Flower longevity on plant: Approximately 1 week for individual flowers.
Persistent or self-cleaning: Self-cleaning.
Flower size:
- *Length*.—Approximately 3.4 cm.
- *Width*.—Approximately 4.9 cm.

Bud:
- *Shape*.—Oblong, with an inflated sphere at terminal end.
- *Length*.—2.7 cm.
- *Diameter*.—1.6 cm.
- *Color*.—Near RHS Green-White 157A.

Corolla:
Petals (measured from separation at top of tube):
- *Number*.—4.
- *Length*.—Approximately 2.0 cm.
- *Width*.—Approximately 2.0 cm.
- *Shape*.—Broad deltoid to somewhat orbicular.
- *Aspect*.—Slightly upwardly cupped.
- *Margin*.—Entire.
- *Texture*.—Glabrous, all surfaces.

*Appearance*.—Iridescent.
*Apex*.—Obtuse.
*Color*.—When opening: Upper surface: Near RHS N155B, faint veins near Red-Purple 62D. Lower surface: Near RHS N155B, faint veins near Red-Purple 62D. Fully opened: Upper surface: Near RHS N155B, faint veins near Red-Purple 62D, but lighter. Lower surface: Near RHS N155B, faint veins near Red-Purple 62D, but lighter.
*Fading*.—Upper surface: Near RHS N155B. Lower surface: Near RHS N155B.

Calyx:
*Form*.—Funnelform base, separating approximately 25% from base, to flare out into 4 large decorative deltoid shaped sepals.
*Fused section*.—Length: Approximately 0.9 cm. Diameter: Approximately 0.7 cm.
*Unfused section*.—Length: Approximately 2.8 cm. Diameter: Approximately 1.5 cm.
*Sepal texture*.—Glabrous all surfaces.
*Appearance*.—Irridescent.
*Apex*.—Acute.
*Color*.—Upper Surface: Near RHS White N155B, flushed Red-Purple 62D. Lower Surface: Near RHS White N155B, flushed Red-Purple 62D.

Fragrance: None.

REPRODUCTIVE ORGANS

Stamens:
*Number* (*per flower*).—8.
*Filament length*.—Average 2.5 cm.
*Filament color*.—Near RHS Red-Purple 62D.
*Anthers*.—Shape: Globular. Length: Approximately 0.1 cm. Color: Near RHS Orange-White 159C.
*Pollen*.—Amount: Not present.

Staminoid structures:
*Number* (*per flower*).—4.
*Length*.—Average 1.6 cm.
*Color*.—Near RHS Red-Purple 62D.

Pistils:
*Quantity per flower*.—1.
*Length*.—Approximately 5.2 cm.
*Style*.—Length: Approximately 4.7 cm. Color: Near RHS Orange-White 159C.
*Stigma*.—Shape: Linear. Color: Near Red-Purple 62D. Ovary: Length: Approximately 0.5 cm. Diameter: Approximately 0.2 cm. Color: Near RHS Yellow-Green 144C.

OTHER CHARACTERISTICS

Seeds and fruits: Not observed to date.
Disease/pest resistance: Neither resistance nor susceptibility to normal diseases and pests of *Fuchsia* has been observed.
Temperature tolerance: Tolerates temperatures from approximately −1 C. to 38 C.
Drought tolerance: No tolerance for drought.

What is claimed is:

1. A new and distinct cultivar of *Fuchsia* plant named 'FWUWW22-0' as herein illustrated and described.

* * * * *